US008652056B2

(12) United States Patent
Edgerley

(10) Patent No.: US 8,652,056 B2
(45) Date of Patent: Feb. 18, 2014

(54) DEFLATION CONTROL VALVE

(75) Inventor: David Anthony Edgerley, London (GB)

(73) Assignee: A. C. Cossor & Son (Surgical) Limited (GB)

( * ) Notice: Subject to any disclaimer, the term of this patent is extended or adjusted under 35 U.S.C. 154(b) by 1186 days.

(21) Appl. No.: 11/751,693

(22) Filed: May 22, 2007

(65) Prior Publication Data
US 2007/0276268 A1 Nov. 29, 2007

(30) Foreign Application Priority Data

May 24, 2006 (GB) .................................. 0610300.6
Mar. 5, 2007 (GB) .................................. 0704186.6

(51) Int. Cl.
A61B 5/02 (2006.01)
F16K 15/14 (2006.01)
F16K 31/44 (2006.01)

(52) U.S. Cl.
USPC .............................. 600/498; 137/845; 251/82

(58) Field of Classification Search
USPC .......... 600/481, 485, 490–502; 137/522, 523, 137/845; 251/82, 118, 88
See application file for complete search history.

(56) References Cited

U.S. PATENT DOCUMENTS

| 3,504,663 | A | * | 4/1970 | Edwards ....................... 600/498 |
| 3,954,099 | A | * | 5/1976 | Raczkowski et al. ......... 600/498 |
| 4,198,031 | A | * | 4/1980 | Ezekiel et al. ................ 251/117 |
| 4,200,259 | A | * | 4/1980 | Ueda ............................. 251/285 |
| 4,237,925 | A | * | 12/1980 | Urushida ....................... 137/552 |
| 4,424,058 | A | * | 1/1984 | Parsons et al. ................ 604/118 |
| 4,497,323 | A | * | 2/1985 | Matsuura et al. ............. 600/498 |
| 4,918,031 | A | | 4/1990 | Flamm et al. |
| 5,026,020 | A | * | 6/1991 | Betush ............................. 251/5 |
| 5,143,077 | A | * | 9/1992 | Kobayashi .................... 600/490 |
| 5,833,620 | A | * | 11/1998 | Murakami et al. ............ 600/498 |
| 6,346,082 | B1 | * | 2/2002 | Negishi ......................... 600/490 |
| 2006/0155197 | A1 | * | 7/2006 | Kishimoto et al. ........... 600/498 |
| 2006/0264765 | A1 | * | 11/2006 | Cha et al. ...................... 600/485 |
| 2007/0239042 | A1 | * | 10/2007 | Takahashi ..................... 600/498 |

* cited by examiner

Primary Examiner — Navin Natnithithadha
Assistant Examiner — Michael R Bloch
(74) Attorney, Agent, or Firm — McKee, Voorhees & Sease, P.L.C.

(57) ABSTRACT

A deflation control valve that automatically varies the rate of gas flow through said control valve to maintain a constant deflation rate during the deflation or exhaust of gas held in a closed pressurisable vessel to which said valve is connectable, wherein said control valve is manually adjustable to set the deflation rate.

19 Claims, 20 Drawing Sheets

DEFLATION CONTROL VALVE

CROSS-REFERENCE TO RELATED APPLICATIONS

This application claims priority to UK 0610300.6 filed May 24, 2006 and UK 0704186.6 filed Mar. 5, 2007, which applications are hereby incorporated by reference in their entirety.

The present invention relates to a deflation control valve for a sphygmomanometer. The valve of the present application is a deflation control valve particularly but not exclusively for use with our latest sphygmomanometer monitor (which is sold under the name "Greenlight") which is to replace mercury and Bourden manometers and which is an accurate: self calibrating electronic manometer. Mercury is no longer acceptable for blood pressure measurement and Bourden gauges, though cheap and small: lose calibration fairly quickly. Automatic sphygmomanometers do not use the auscultatory technique and clinicians have concerns about their accuracy and appropriateness. Our new electronic manometer provides an effective solution. However, our new monitor demands more from the deflation control valve. The monitor incorporates a deflation rate indicator. Standards set an acceptable deflation rate (2 mmHglsec) for the measurement of blood pressure in the systolic and diastolic pressure zones and this deflation rate is indicated on our monitor. The valve has to be accurate and controllable enough to allow clinicians to adjust the deflation rate easily to the correct value. This is made more difficult as the volume of air held in the electronic monitor is small compared to that held in a mercury sphygmomanometer and the valve has to be able to control smaller air flow rates for a given deflation rate than when used with a mercury sphygmomanometer.

There are two types of deflation valve commonly in use, needle valves and sleeve/piston valves. Needle valves are the most widespread; they do not give sufficiently precise control of the deflation rate at such low air flow to be able to set it easily to 2 mm Hg/sec. Sleeve valves are better, but neither type compensate for reducing flow rate as the cuff pressure drops or give a tactile indication of the setting zone.

After development of the valve of the present invention, there was discovered U.S. Pat. No. 4,198,031 of Gulf & Western Industries which discloses an automatic air deflation valve for use with a sphygmomanometer and comprising a housing having an air flow channel extending through the longitudinal extent thereof and at least one air deflation port extending outwardly from said channel. The port includes a deformable diaphragm, which may be two part, sealingly supported only on its outer edges and otherwise without restraint and having a central aperture extending through the thickness thereof. The diaphragm and aperture are adapted to deform in accordance with the air pressure applied against it from said channel to automatically adjust the size and shape of said aperture, thus producing a constant air deflation rate therethrough. The valve has an override (dump) valve for fast deflation; it is not adjustable for different deflation rates, cuff or arm sizes. The valve cannot be closed, has no manual control or adjustment and appears to be designed for use on automated devices.

Features sought in an improved deflation control valve includes any of the following considerations:

1. The valve has to be sensitive and accurate enough to set the deflation rate correctly.
2. The valve needs to be able to maintain the deflation rate consistently as the pressure in the cuff and monitor is dropping. The valve should compensate for the reducing pressure in the measurement zones, keeping the deflation rate as constant as possible and allowing the clinician to concentrate on the diagnosis rather than the manipulation of the valve.
3. Clinicians need to be able to find the correct valve position quickly at the systolic and diastolic pressures and to increase airflow easily outside these pressure zones so that the cuff remains inflated on a patient's arm for as short a period as possible. Some tactile features that help the clinician find the operating zone of the valve will be helpful.
4. The relationship between the angular position of the knob and the deflation rate should be perceived by the clinician as proportional and easily controlled. The rotation of the knob to vary the deflation rate from 2 mm Hg per second to say 8 mm Hg per second for the smallest cuff size should ideally be similar to that needed to vary the deflation rate of the largest cuff size over the same range (though it is likely that the absolute position of the knob to achieve a given flow rate will vary according to cuff size). The valve should also be able to be opened and closed fully quickly—the knob rotation from the start or end of the adjustment zone to the fully open or fully closed position should be appropriate. These requirements indicate that the relationship between the angular rotation of the knob and the position of the platen is unlikely to be either linear or directly proportional.
5. The valve should connect to other components in the system with a push taper connection.
6. The valve, though precise and accurate must be robust in use.
7. The valve should be as small as possible.

A number of different methods of controlling air flow were considered in the evolution of the present invention including accurate needle valves controlled by a more precise mechanism, improved sleeve valves and face valves. Of the types considered, it was discovered face valves offered a way of compensating flow rate for diminishing pressure in the cuff and keeping a steady deflation rate without continual adjustment of the valve. They also seemed effective at controlling low air flow rates. A number of test rigs were made to learn more about the behavior of face valves.

According to the present invention there is provided a deflation control valve according to claim 1. Also according to another aspect of the invention there is provided a deflation control valve in the form of a face valve for a sphygmomanometer comprising a valve body having a first outlet passage connectable to be communicatable with a pressurisable tube connected to a cuff of a sphygmomanometer and an inlet passage connectable to a rubber bulb pump or like inflation means, said valve body defining a valve chamber in which a flexible diaphragm is provided partially or substantially closing the chamber and said diaphragm having a deflation, airflow passage which on one side of the diaphragm is in communication with said inlet and outlet passage and, on the opposite side of the diaphragm, is in communication with an exhaust outlet or atmosphere and is closeable or partially closeable during inflation by a displaceable closure disc, plate or platen which is releasably held in the closing position against said passage by a manually operable, controllable or adjustable release means.

The flexible diaphragm is preferably resilient.

Preferably the manually operable release means is a reversibly rotatable and axially displaceable control knob bearable on the platen, or such is a non-axially displaceable rotary knob with cam and lever means for reversibly urging the platen into a closing position. Preferably the displacement means associated with the knob (such as a screw thread or tapered cam surface) is geared such that the movement is amplified and thus greater movement of the knob enables a smaller movement of the disc or platen.

Preferably the platen and/or diaphragm has an air escape passage or means which varies in cross-section as the pressure under the diaphragm is reduced and which can be controlled by lifting and lowering the platen. It is alternately or additionally possible for air escape means to be provided on/in the diaphragm as indicated. Preferably this escape passage is provided by a recess and preferably a small groove or channel or other airflow control enhancing feature on or in its surface facing said diaphragm to compensate, in use, for falling pressure in the cuff and enable the deflation rate to be controlled. The groove is preferably elongate and diametrical and central and of differing cross-sectional area, largest in the center of the platen and reducing to zero nearer to the edge of the platen. Preferably the disc or platen has a flat normally lower surface in which the groove is also located and the root of the groove is curved. Instead of an elongate groove, a recess of other shape may be provided. Other airflow control enhancing features preferably additionally or alternatively include the surface finish of the platen and/or the diaphragm and/or the shape of both parts and/or the softness and/or thickness of the diaphragm.

Thus in its broadest aspect here compensating means are provided to enable the restriction or opening of the path between the diaphragm and platen to achieve a compensating affect using the changing curvature of the diaphragm and thus may be by way of the means indicated above e.g. by forming on the platen and/or diaphragm.

When the valve is closed, this exhaust hole or port is sealed or substantially closed by the disc or platen, which is held down by means extending from the release means which is preferably an axially displaceable rotary knob secured with a fine screw thread to the valve body or a non-axially displaceable rotary knob having a cam which acts on lever means to achieve the same effect. When the release means is in such position, the pressure in the cuff and monitor can be raised by pumping the inflation means typically to above systolic pressure. The relationship between the platen and diaphragm is preferred such that releasing the release means slightly, allows the platen to rise and air can seep from (the high pressure area) of the valve/chamber thereon through the port in the diaphragm and between the face of the platen and diaphragm to atmosphere to allow the pressure of the cuff and monitor to drop. Adjusting the release means, normally by rotation, to open and closed positions or intermediate positions controls the rate at which air flows through the valve.

It is to be appreciated that an air passage is created between the diaphragm and platen which varies in size depending on the pressure on the diaphragm (and unlike the mentioned U.S. prior art, not solely dependent on the deformation of the hole in the diaphragm). The groove is formed in the platen as an open channel of varying/differing cross-section and which is partially closed by contact with the diaphragm. The amount of groove sealed by the diaphragm is desirably controlled by the curvature of the diaphragm (created by the cuff pressure) and the position of the platen. Altering the position of the platen allows the flow rate through the valve to be adjusted for different cuff and arm sizes. The preferably elastomeric diaphragm and the platen are such that the diaphragm will, if not constrained by the platen, lift (be deformed) by the cuff air pressure. If the cuff is pressurized and the platen is raised, the diaphragm will tend to follow the platen, closing the air passage formed in the groove between the diaphragm and the platen by an amount proportional to the difference between the cuff pressure and atmospheric pressure. As the pressure in the cuff drops, the diaphragm will deform less, exposing more of the groove formed in the platen to atmosphere and opening the air passage formed in the groove between the platen and diaphragm, slightly and compensating for the falling pressure in the cuff. The screw action and the cam arrangement embodiments give the clinician a familiar action, a proportional response—more rotation, more flow—allowing the flow rate to be adjusted as required. Pressure compensation matches the chosen flow rate. The clinician can stop the flow or open it partially or fully. The components are also easy to mould—an open slot rather than a fine hole. The advantages of the valve of the present invention resides in its great simplicity, and enables the valve to be shut off or fully opened and to have one knob that controls everything.

Click or pawl and ratchet means associated with the release means regulate the movement of the control knob and provide audible and/or physical feedback to the clinician.

BRIEF DESCRIPTION OF THE DRAWINGS

The invention will be described further by way of example, with reference to the accompanying drawings, in which.

DETAILED DESCRIPTION OF THE PREFERRED EMBODIMENT

Figure 5:
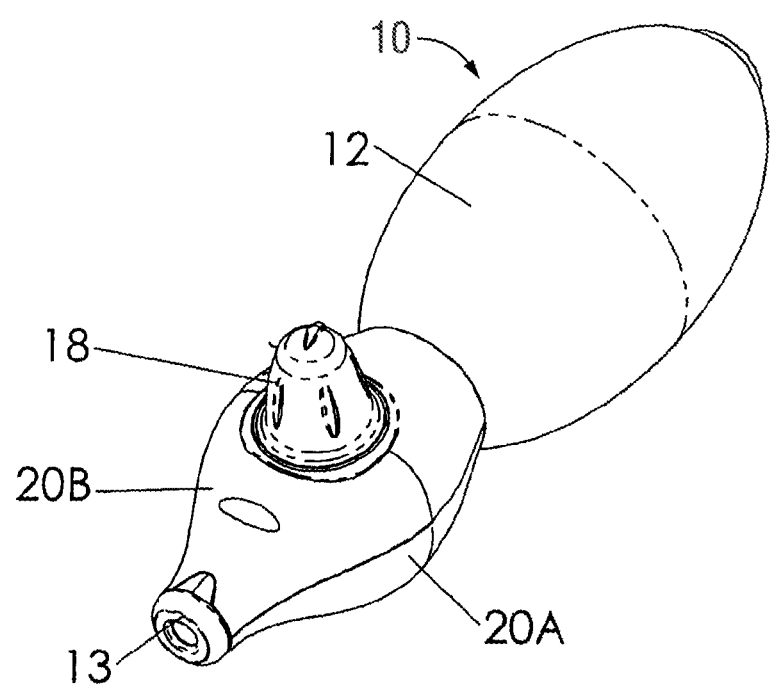
FIG. 5 is a perspective view of a second deflation control valve forming a preferred embodiment of the invention.
Figure 6:
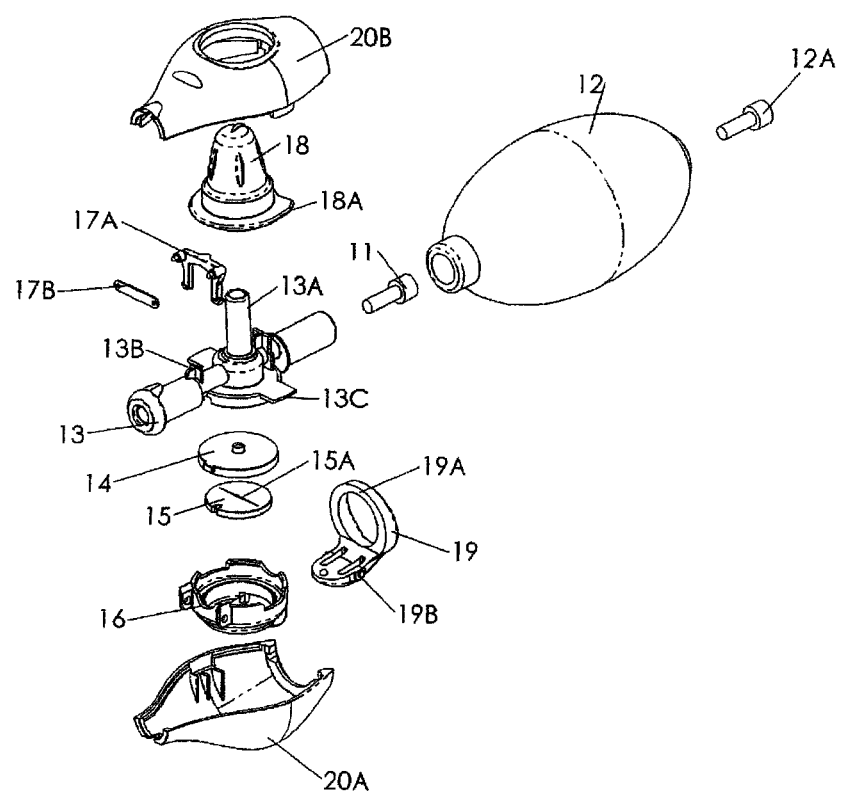
FIG. 6 is an exploded perspective view of the valve of FIG. 5.
Figure 6A:
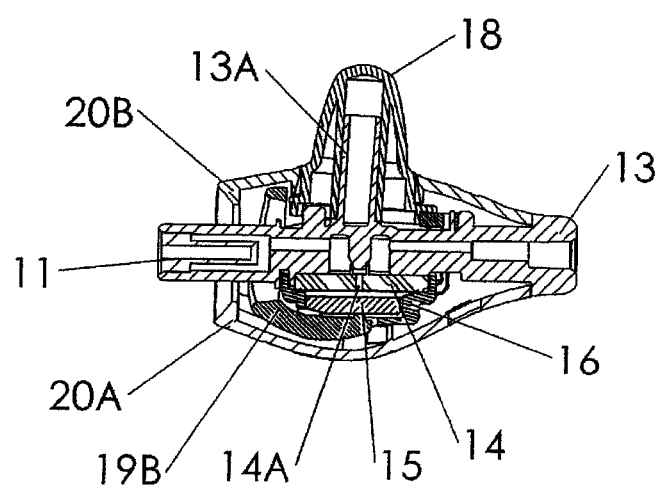
FIG. 6A is a longitudinal cross section through the valve of FIGS. 5 and 6.
Figure 6B:
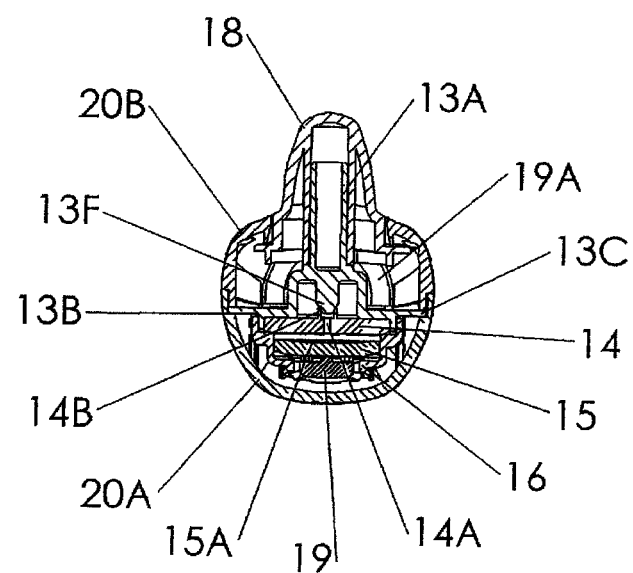
FIG. 6B is a transverse section through the valve of FIGS. 5 and 6.
Figure 7:
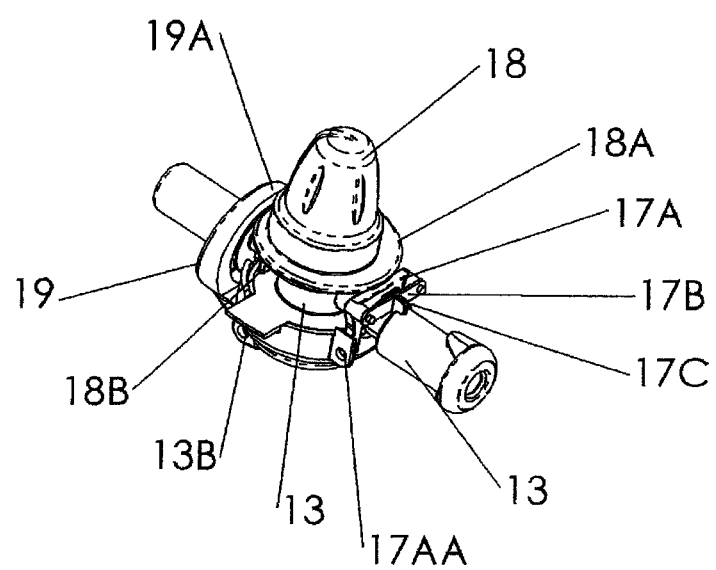
FIG. 7 is a perspective view from the cuff attachment and of the valve of FIGS. 5 and 6 but without the inflation bulb and without the body halves and showing the cam in the maximum displacing and valve traveling position (the knob is in the fully closed position)

A rubber squeeze-bulb 1 (only shown in part but similar to bulb 12 in FIGS. 5 and 6) is provided for inflating a cuff 100 of a sphygmomanometer and is provided in known manner with an inlet aperture at one end for receiving a one-way inlet valve (not shown). At the opposite end outlet side of bulb 1 there is an outlet sleeve portion 1A sealed around a one way rubber valve or check valve 2 contained in an inlet of a valve body 3. The inlet of body 3 leads into the valve chamber formed by the valve body 3 having a tubular upper portion forming a seat for a flexible valve member or diaphragm 4. An outlet 3A leads to the cuff. Elastomeric disc-like diaphragm 4 (about 45 shore A material), is seated in the body 3 and sealed at its periphery against the seat by means of a sealing cap 6 including an externally threaded tubular portion which is threadingly engaged and secured in an upper portion of valve body 3 and urges the diaphragm 4 into sealing engagement with its seat. The cap 6 has a central aperture 6A for exhaust of air from the valve when opened and to enable a pin or boss to extend therethrough to act on the diaphragm 4 via a disc or platen. Diaphragm 4 has a central passage or hole or port 4A for flow of air which is controlled/stopped via a disc like platen 5. A rotary control knob 8 is provided threadingly mounted on valve body 3 which has a fine thread and axially displaceable by rotation to move towards and away from the platen 5. Knob 8 has a platen engagement pin or boss 8A on its lower inner side forming a control portion of the knob as it extends through aperture 6A in cap 6 and may bear against the upper surface of platen 5. A metal click spring 7 is mounted on the top of cap 6 on two retaining pins 6B, 6C extending through spring holes 7B and the knob 8 has a circle of serrations on its inner side engageable by a pawl portion 7C of spring 7. Click spring 7 and in particular pawl or dimple portion 7C operates against the ridges or serrations 8B on the underside of the knob 8. Spring 7 comprises two spaced apart flap-like portions 7D lying in the same plane and from which, in its position of use, two yoke-like springs arm portions 7E extend inclined downwardly to two spaced apart flat web-like mounting portions 7F both lying in the same plane and in which holes 7B are found. The small dimple 7D on one portion runs against the cap serrations 8B to create the click action. The other portion 7D also runs against the cap surface but on a smooth section inboard of the serrations. The spring 7 pivots against the clamp on the portion 7F of its surface with the two holes 7B and the cap 6 presses against both the bottom and top legs of the spring, ensuring the spring dimple clicks against the cap serrations. The platen/lever/cam assembly have the capability of closing the valve completely.

Air from the atmosphere is pumped into and through the valve body 3 by the rubber bulb 1, entering through the one way valve 2. The outlet of the body 3 has a rubber tube 3A running to the manometer and cuff. Diaphragm 4 is sealed to valve body 3 around its periphery by cap 6. There is a second outlet from valve body 3 via the port 4A in the center of diaphragm 4 for exhausting/deflating the cuff. When the valve is closed, this exhaust hole or port 4A is sealed or substantially closed by platen 5, which is held down by the boss 8A on knob 8 which secured with a fine screw thread to valve body 3. When knob 8 is screwed closed (down), the pressure in the cuff and monitor can be raised by pumping bulb 1, typically to above systolic pressure. Unscrewing knob 8 slightly allows platen 5 to rise. Air can seep from valve body 3 (the high pressure area) through port 4A, along the passage formed by the groove 5A in the platen, between the face of platen 5 and diaphragm 4 and through a hole in the knob 8, or otherwise to atmosphere, allowing the pressure in the cuff and monitor to drop. Opening and closing knob 8 controls the rate at which air flows through the valve.

A second effect provides pressure compensation. The underside of diaphragm 4 is subject to cuff pressure. The elastomeric diaphragm 4 will, if not constrained by the platen, lift (be deformed) by this pressure. If the cuff is pressurized and the platen 5 is raised, the diaphragm will tend to follow the platen, exposing the groove formed in the platen that connects port 4A to atmosphere by an amount proportional to the difference between the cuff pressure and atmosphere. As the pressure in the cuff drops, the diaphragm will deform less, increasing the size of the air passage leading from port 4A via the platen groove to atmosphere by exposing a section of the groove in the platen with a wider cross-sectional area. This effect, if correctly exploited, will compensate for the falling pressure in the cuff and mean that a clinician, once the correct flow rate has been achieved, will not have to continue to adjust the valve as the pressure drops.

It has been discovered that this effect is influenced by the surface finish of the platen and diaphragm, the shape of both parts and the softness of the diaphragm. Difficulties can be experienced achieving a precise control of the deflation rate and compensate for pressure effectively using a flat diaphragm and platen. The valve may tend either not to compensate enough for pressure (operate like a needle valve) or to overcompensate and increase flow rate dramatically as the pressure dropped. It has been discovered that adding a small groove 5A to the face of the platen overcomes these difficulties and makes the compensation work well and the airflow control accurate and provides a preferred embodiment. The groove 5A is at its deepest and widest over port 4A and tapers to nothing about 5 mm either side of port 4A.

The amount of the groove 5A revealed by the diaphragm defines the size of the gap through which air can flow, the more the diaphragm bulges, the more of the platen face it covers and the smaller the passage for air to flow through. This additional feature is easily mouldable and makes the pressure compensation and flow control much more reliable and precise. Good compensation can be achieved by choosing the correct groove profile, diaphragm material, thickness and texture and overall geometry.

One of the characteristics of a face valve is that very small movements of the platen can have a large effect on airflow. The elasticity of the diaphragm and the application of pressure to most of its under surface (causing it to bulge under pressure) increase the amount of movement needed to change the air flow rate. The provision of a groove or slot helps further. It is desirable that the screw thread should have some tolerance, and gripping the knob in different ways can also significantly affect the flow rate through the valve. A screw thread gives a linear relationship between the rotation of the knob and its axial movement. This is not helpful when designing one valve to cope with different cuff and patient sizes— much more air needs to flow from a large cuff on a large patient than a small cuff on a child to deliver the same deflation rate. Nor does the clinician want to turn the knob 8 far to shut off or fully open the valve (both actions are needed during a blood pressure test).

Figure 1:
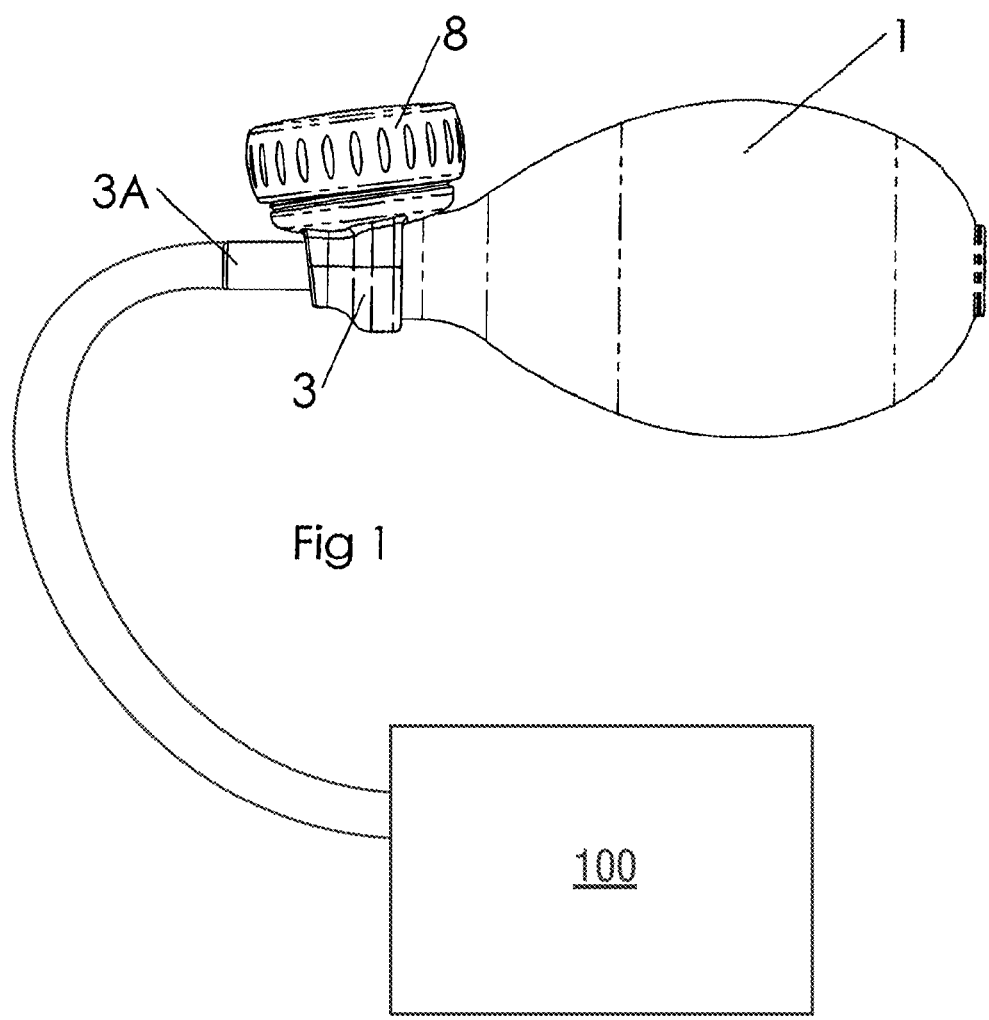
FIG. 1 is a side elevation of a first embodiment of a control valve of the present invention.
Figure 1A:
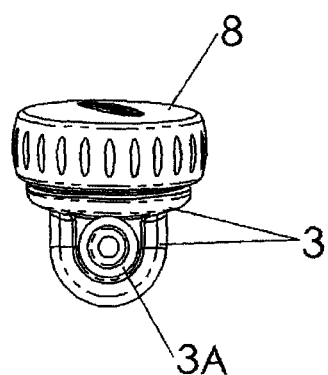
FIG. 1A is an end elevation of the valve of FIG. 1.
Figure 1B:
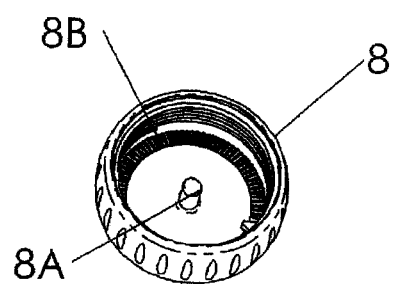
FIG. 1B is a perspective view from below of the control knob of FIGS. 1, 1A or 4.
Figure 1C:
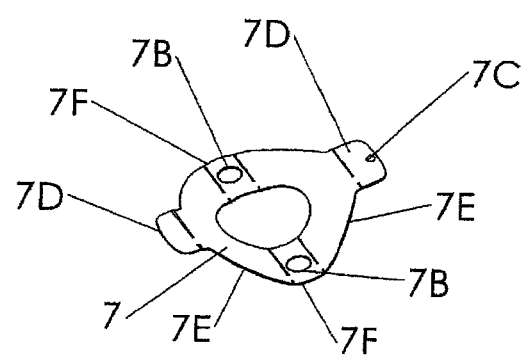
FIG. 1C is a perspective view of a click spring.
Figure 2:
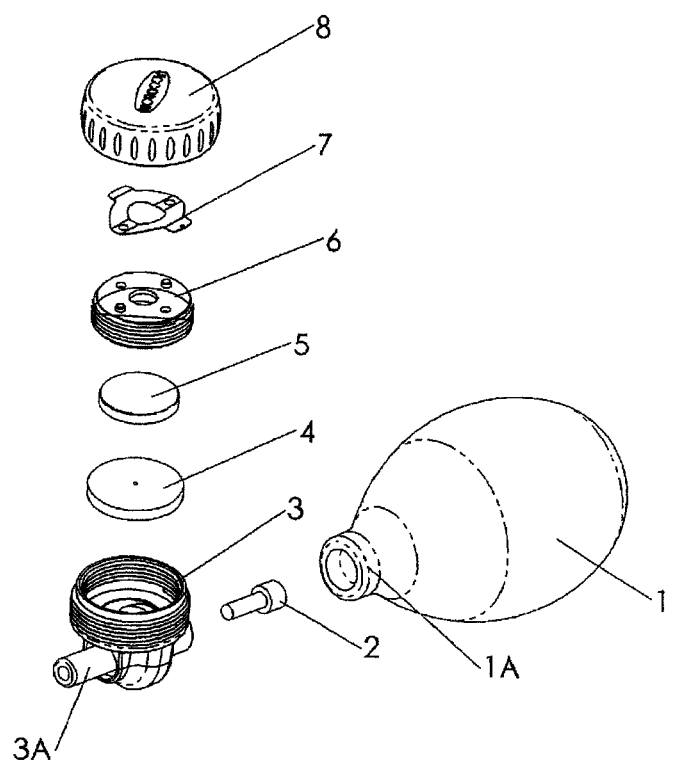
FIG. 2 is an exploded perspective view of the components of the device of FIGS. 1, 1A and 4.
Figure 3:
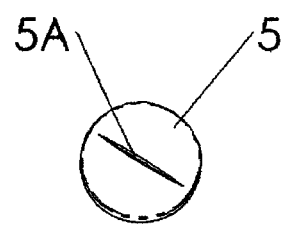
FIG. 3 is a perspective view of the underside of the preferred construction of the control disc or closure platen for use in the embodiments of FIGS. 1, 1A and 2 and 4 or FIGS. 5 to 15.
Figure 4:
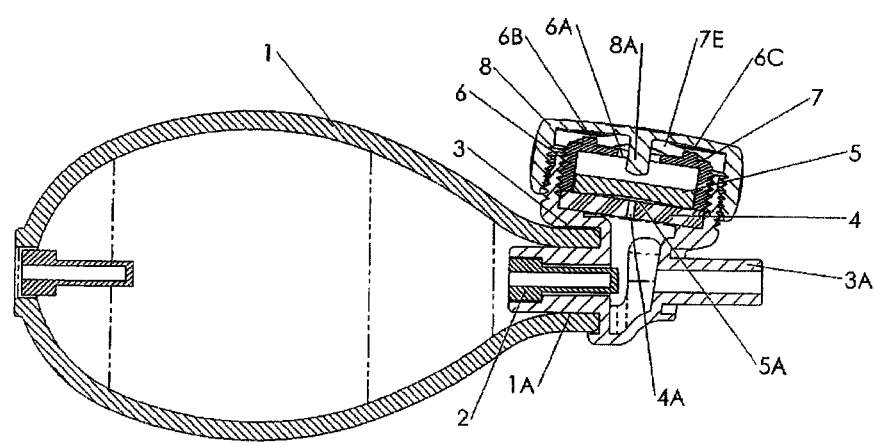
FIG. 4 is a cross section on the line A-A of FIG. 1A through the deflation control valve with rotary knob adjustment and shown partly connected downstream to a squeeze-bulb.

A second and preferred embodiment of deflection control valve 10 is illustrated in FIGS. 5 to 15 wherein a known rubber squeeze inflation bulb 12 is provided with inlet check valve 12A at its inlet end and connected at its outlet end via check valve 11 to the inlet portion of the valve body 13 which has knob-mounting spindle 13A extending from the top thereof and, like in FIG. 4, defines a seat in a chamber on one side of its air through-flow passage and on which seat a diaphragm 14 is clamped by means of a clamp 16 which snap-fits onto the body 13 sealing the diaphragm 14 against the seat.

Diaphragm 14 has a central aperture or port 14A similar to that described previously and communicates the through-flow passage with the upper side of the diaphragm from whence air under pressure may escape to atmosphere. A disc or platen 15 is provided identical or similar to platen 5 described previously with a double tapered groove 15A part way along its diameter as described previously. Platen 15 is releasably urgeable against diaphragm 14 to close or partially close aperture 14A by means of a lever 19 which has an annular or ring-like portion 19A on which a cam 18A of raising knob 18 may slidingly act, and has a plate-like portion 19B which is displaceable in aperture 16A of clamp 16 to act on platen 15. Lever 19 is a pivotally mounted at 19B on clamp 16. Clamp 16 has diametrically opposite recesses 16B, 16C in which flanges 13B, 13C of the valve body 13 locate to prevent relative rotation. Two clam shells on upper and lower cases 20A, 20B, clamp together and hold knob 18 rotatable on spindle 13A.

The disk or platen 15 (identical or similar to platen 5 described previously) is controlled by the action of the cam 18A on the face of the knob 18 which is rotatable on spindle 13A. This cam 18A is preferably shaped so that the valve behaves to the user in an apparently linear way in the adjustment zone, does not have to be turned much more for large cuffs than for small, or to reach closed and fully open states. Placing the knob on the opposite side of the valve the platen 15 and the diaphragm 14 brings a number of advantages. Mechanical advantage can be built into the lever 19 that transmits the cam 18A movement to the face of the platen 15, so that there is more travel at the knob cam 18A than at the platen 15—this helps reduce the effect of knob bearing tolerance and any sideways movements of the knob caused by the clinicians holding the valve in unexpected ways.

Any axial movement of the knob which is more difficult to control does not affect the position of the lever or platen. The knob bearing shaft or spindle 13A is mounted directly to the back of top face of the valve body and is provided with rotation stops 13E, and knob 8 is located axially between abutment surfaces on the valve body and on the inside of case 20B so that the knob can be handled reasonably roughly without applying forces to the valve mechanism. A click action (click 17A and metal click spring 17B operating on knob ridges 8B) can also be assembled easily in such a way that the forces generated by the spring 17B and click 17A do not affect the position of the lever 19 or platen 15. The diaphragm 14 is sealed to the body with snap-fit clamp 16. Clamp 16 also provides a pivot 19B & C for lever 19 and pivot 17AA for click 17A. The two body halves 20A and 20B, protect the mechanics of the valve.

Figure 8:
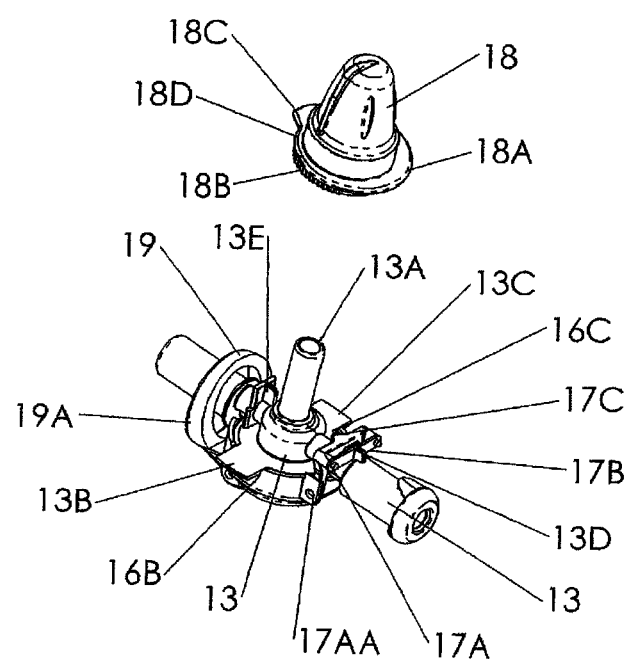
FIG. 8 is a view similar to FIG. 7 with the knob raised.
Figure 9:
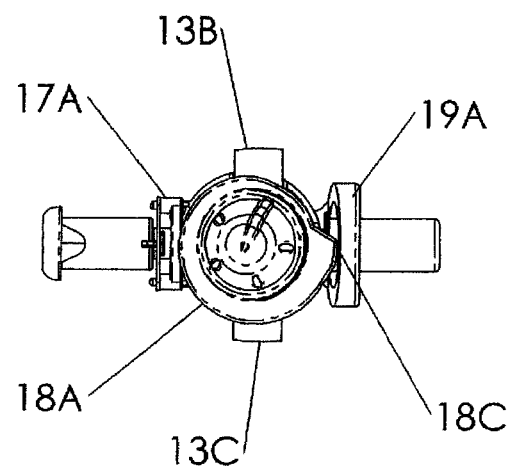
FIGS. 9 and 10 are reversed plan and perspective views from below of the part of the valve of FIGS. 7 and 8 but turned through 180° and without body halves (20a, 20b) still in the maximum lever displacement by the control of the rotary knob.
Figure 10:
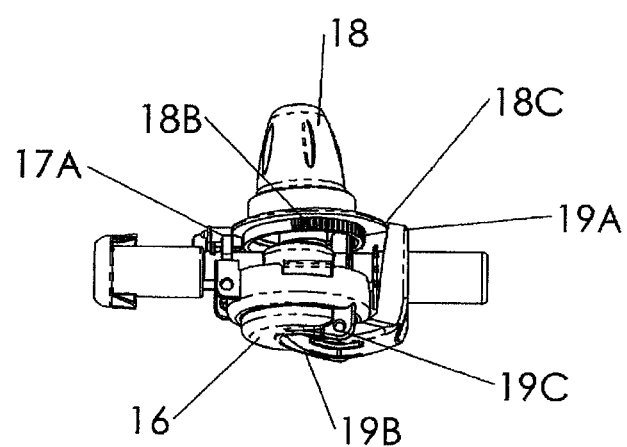
Figure 11:
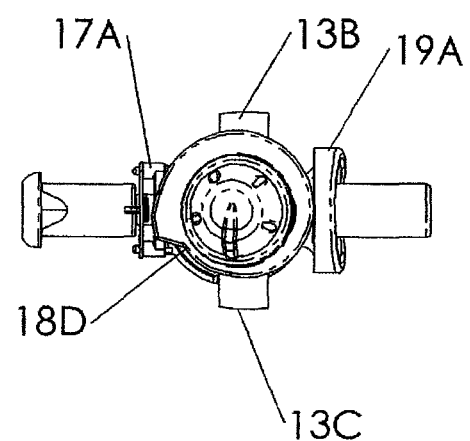
FIGS. 11 and 12 are similar views to FIGS. 9 and 10 but at an intermediate position of adjustment.
Figure 12:
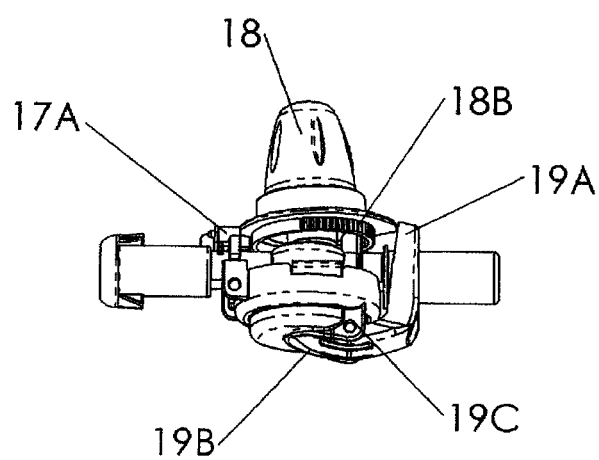
Figure 13:
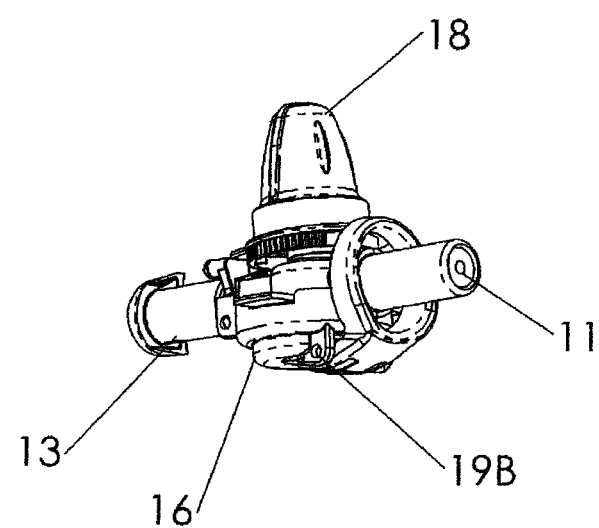
FIGS. 13 and 14 are opposite end views of the valve in the position as shown in FIGS. 11 and 12.
Figure 14:
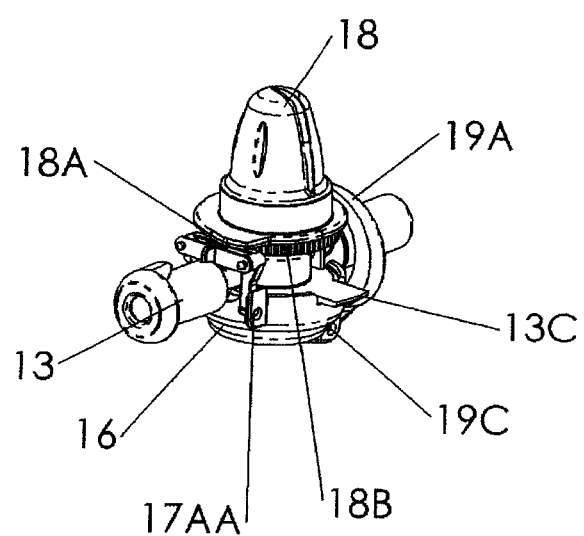
Figure 15:
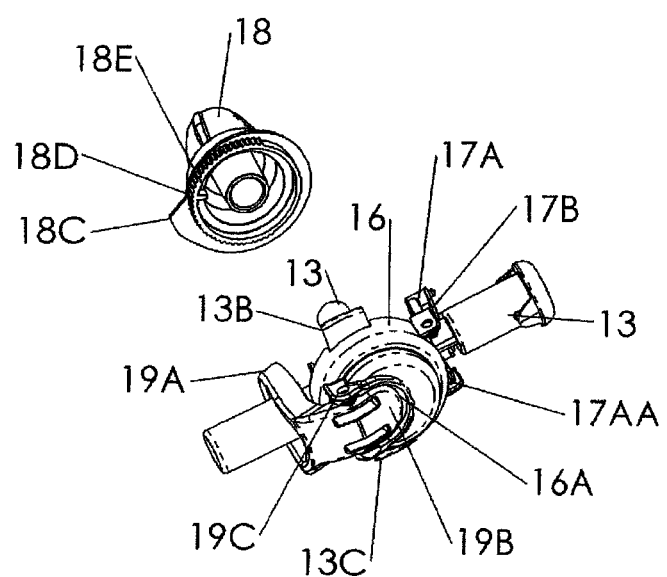
FIG. 15 is a perspective view from below the components shown in the condition of FIG. 8.

The rotary knob 18 turns freely on the spindle 13A (through approximately 310° as controlled by stop 13E (FIG. 8). The cam is radially tapered and moves lever 19 which acts on the platen 15 and therefore on diaphragm 14. Lever 19 pivots in bearing holes 19B & C in clamp 16. The platen 15 is not scalingly mounted to the valve body. The diaphragm 14 is sealed to the body by a periphery at edge of clamp 16, which snaps onto the body 13. Air cannot escape from the valve body through hole 14A in the diaphragm to atmosphere when the diaphragm is pressed flat against the valve body by the platen (the platen is forced against the diaphragm by the lever 19 and knob cam 18A). The diaphragm 14 seals against the platen 15 around the periphery of the platen (not a particularly good seal) and also against the spigot 13F formed in the center of the valve body (which contacts the raised annular wall 14B on the diaphragm 14—this thin wall 14B reduces the force needed to seal the diaphragm and reduces the likelihood of parts creeping over time if the valve is left tight shut for long periods).

When the knob 18 is turned and the platen 15 allowed to lift away from the valve body, the pressure in the valve flexes the diaphragm 14 and lifts the platen 15. The diaphragm 14 flexes at its center (it is held around its periphery), and an escape path is created for the pressurized air in the valve body past the thin sealing rib on the diaphragm and the valve spigot, through the hole in the center of the diaphragm, down the two passages formed between the platen groove and the diaphragm and, if the curvature of the diaphragm is sufficient, to atmosphere. The more the diaphragm is curved (flexed), the more of the ends of the platen groove are revealed and the larger the air escape path cross section becomes. The diaphragm curvature depends on the position of the platen (controlled by the cam and lever) and on the pressure drop across the diaphragm (as mentioned previously, the higher the pressure in the valve, the greater the diaphragm deflection, the more the platen groove is covered, the smaller the air escape orifice—hence pressure compensation).

Whilst there is axial movement of the knob in the first embodiment there is no movement along the axis of rotation in this second embodiment merely about said axis. Thus it is possible to have whatever desired relationship between the knob rotation and platen movement thereof, (if need not be linear, and can be adjusted so that the relationship between the knob rotation and deflation rate (rather than platen movement) appears linear to the user). The knob bearing is easy to form, the knob can be robust, the delicate mechanics of the valve protected and a tactile 'click' is provided.

The click action of the tactile means is created here by a flat spring, trapped at its center on the valve body (the post-like moulding 13D locates the click spring) driving the plastic pawl 17C (called the click) against serrations or ridges 18B. The pawl 17C is pivoted on the clamp 16 to prevent any sideways movement. The reason for using a plastic pawl 17C (rather than simply having a detail on the spring that engages on the ridges 18B on the underside of the knob 18) is to control the feel of the click with greater accuracy—these clicks happen every 6° of knob rotation, which is a small movement to identify with the click. The shape of the ridges on the underside of the knob and the co-operating boss on the face of the plastic pawl or 'click' component create the feel. The ridges do not cover all the rotation of the knob—they define the 'working zone'.

Taking the knob zero point (cam point 18C against 19A) as being when the valve is fully shut off, the first click is felt after 48° of rotation. With the smallest cuff size used on a child, the correct deflation rate for reading systolic or diastolic blood pressure will be reached after about 6 clicks, or a further 36° rotation (at normal room temperature). The knob is turned a further 15 or so clicks (approximately 90°) to deflate the cuff reasonably fast between measuring points. The correct deflation rate for measuring the blood pressure of an obese adult is reached about 15-20 clicks in (rather than 6 for a child). A total of 38 clicks (or 228° of rotation) has been provided, so that a clinician should in most cases be working within the 'click' zone while taking pressure readings and moving between measuring points. Once the blood pressure has been measured, the valve is opened fully to give the quickest deflation. The valve is fully open (18D adjacent 19A) when the knob is rotated 310° from the zero (or closed) position and the last 34° of valve movement have no clicks. One stop for knob rotation is provided—it can be seen on the valve body on the bulb side of the knob spindle 13A and there is a corresponding rib 18E on the underside of the knob.

Thus in summary, the present invention provides an adjustable face valve connectable to a pressurisable cuff or other vessel to control air flow from the cuff, preferably with pressure compensation such that valve automatically maintains a constant rate of pressure change in the cuff for a given setting of the valve regardless of the pressure in the cuff, the main reason for pressure compensation being to provide the clinician with a valve that does not need to be adjusted as the pressure in the cuff falls. The advantages of driving the platen with a cam, other than the mechanical and structural advantages of the cam arrangement we have arrived at (mechanical advantage, minimal disturbance of the platen position if the user applies pressure to the knob while holding it, disconnection of the more delicate parts of the valve from the user so that they cannot be abused easily), include making the relationship between knob rotation and deflation rate more intuitive to the user—more proportional, which means that the cam profile has to be slightly unusual such that it has a shut off ramp operating to close the valve, which reduces to a very gradual spiral angle at the beginning of the deflation zone (for controlling small cuffs). The spiral angle then increases as the valve is opened further for controlling larger cuffs or quick exhaust.

It is intended the technique of and valve for controlling small air flow with pressure compensation, has applications other than for sphygmomanometers.

What is claimed is:

1. A deflation control valve that automatically varies a rate of gas flow through said control valve to maintain a constant deflation rate during a deflation or exhaust of gas held in a closed pressurisable vessel to which said valve is connectable, wherein said control valve is manually adjustable to set the deflation rate, said control valve comprising:

a valve body having a passage communicable with said pressurisable vessel, said valve body defining a valve chamber communicating with said passage in which a flexible diaphragm is provided partially or substantially closing said valve chamber;

said diaphragm being in sealing abutment with a seat in said valve housing around a periphery of said diaphragm, and forming on an opposing side thereof a part of an exhaust chamber; said diaphragm, in use, being, on a valve chamber side subject to gas pressure in said pressurisable vessel and, on the opposing side, subject to gas pressure in the exhaust chamber, which may be atmospheric pressure;

said diaphragm having an aperture or port extending therethrough, and said diaphragm on one side being in communication with said valve chamber and, on the opposing side, being in communication with said exhaust chamber or atmosphere;

said diaphragm being closeable or partially closeable by a displaceable closure disc, plate or platen that is releasably held by an operable, controllable or adjustable release means in a closing position against said diaphragm to cover said aperture or port, and whereby adjusting said release means to open and closed positions or intermediate positions, controls the deflation rate at which gas flows through the valve via the valve chamber through the aperture or port in the diaphragm and between a face of the closure disc, plate or platen and the diaphragm to exhaust or atmosphere to allow gas pressure of the valve chamber to drop in a controlled manner; and wherein the closure disc, plate or platen and diaphragm have an air escape passage or means which varies in cross-section as the deformation of the diaphragm due to the pressure difference across it and the position of the closure disc, plate or platen varies.

2. The valve as claimed in claim 1, where a resistance to passage of gas from a higher pressure in said valve chamber to a lower pressure in said exhaust chamber is determined by a surface area of said diaphragm in contact with said closure disc, plate or platen, a local contact pressure between said diaphragm and said closure disc, plate or platen and a material, geometry and surface finish of said diaphragm and said closure disc, plate or platen.

3. The valve as claimed in claim 1, in which a manually operable release means is a reversibly rotatable and axially displaceable control knob bearable on the closure disc, plate or platen.

4. The valve as claimed in claim 1, in which a manually operable release means is a non-axially displaceable rotary knob with cam and lever means for reversibly urging the closure disc, plate or platen into a closing position, the cam so formed that there appears to the user to be a linearly (or any other) proportional relationship between the angular position of the knob and the rate of change of pressure difference between the valve chamber and the exhaust chamber.

5. The valve as claimed in claim 4, in which a displacement means is associated with the knob and such displacement means are structured so that a greater movement of the knob enables smaller movement of the closure disc, plate or platen.

6. The valve as claimed in claim 1, wherein alternate air escape control means is provided on or in the diaphragm to compensate for falling pressure in the pressurisable vessel.

7. The valve as claimed in claim 6, in which the alternate air escape means is a small groove or channel or other airflow control enhancing feature on or in the surface of said diaphragm facing said closure disc, plate or platen.

8. The valve as claimed in claim 6, in which a groove is the alternate air escape control means, and wherein the groove is elongate and diametrical and central and positioned over or through the aperture or port perforating the diaphragm and of a varying/differing cross-sectional area, largest in the center of the closure disc, plate, platen, or the diaphragm and reducing to zero nearer to the edge of the closure disc, plate, platen, or diaphragm, such that amount of surface area of the diaphragm in contact with the closure disc, plate or platen determines the minimum cross-sectional area of the groove through which gas escaping from the higher pressure chamber to the exhaust chamber has to flow.

9. The valve as claimed in claim 1, in which the air escape means is an escape passage in the form of a recess to compensate, in use, for falling pressure in the pressure chamber and enable a rate of change of pressure in the valve chamber to be controlled.

10. The valve as claimed in claim 1, wherein alternate air escape control means is provided on or in the closure disc, plate or platen to compensate for falling pressure in the pressurisable vessel.

11. The valve as claimed in claim 10, in which the alternate air escape means is a small groove or channel, or a projection (such as a ridge or bump) or other airflow control enhancing feature on or in the surface of said closure disc, plate or platen facing said diaphragm.

12. The valve as claimed in claim 1, in which airflow control enhancing features are provided additionally or alternatively including a surface finish of the closure disc, plate or platen and/or the diaphragm and/or a shape of both parts and/or a softness and/or thickness of the diaphragm.

13. The valve as claimed in claim 1, in which, in use, when the valve is closed, the diaphragm aperture or port is sealed or substantially closed by the closure disc, plate or platen, which is held down by means extending from the release means.

14. The valve as claimed in claim 13, in which the release means is an axially displaceable rotary knob secured with a fine screw thread to the valve body or a non-axially displaceable rotary knob having a cam which acts on lever means to hold down the closure disc, plate or platen.

15. The valve as claimed in claim 1, in which click or pawl and ratchet means are associated with the release means and regulate a movement of a control knob and provide audible and/or physical feedback to a clinician.

16. The deflation control valve as claimed in claim 1 in combination with a sphygmomanometer.

17. The valve as claimed in claim 1, wherein the closure disc, plate or platen includes a tapered groove in alignment with said aperture or port, the tapered groove being at its deepest and widest at said aperture or port and tapering to narrower widths at opposing ends of the groove.

18. A deflation control valve in a form of a face valve for a sphygmomanometer comprising a valve body having a first outlet passage connectable to be communicable with a pressurisable tube connected to a cuff of a sphygmomanometer, and an inlet passage connectable to an inflation means, said valve body defining a valve chamber in which a flexible diaphragm is provided partially or substantially closing the chamber and said diaphragm having a deflation air-flow passage which on one side of the diaphragm is in communication with said inlet and outlet passage, and on an opposing side of the diaphragm, is in communication with an exhaust outlet or atmosphere and is closeable or partially closeable during deflation by a displaceable closure disc, plate or platen which is releasably held in a closing position against said diaphragm passage by a manually operable, controllable or adjustable release means, wherein the air flow passage is an aperture or port, wherein the closure disc, plate or platen includes a tapered groove in alignment with said aperture or port, the tapered groove being at its deepest and widest at said air-flow passage and tapering to narrower widths at opposing ends of the groove.

19. A deflation control valve in a form of a face valve for a sphygmomanometer comprising a valve body having a first outlet passage connectable to be communicable with a pressurisable tube connected to a cuff of a sphygmomanometer, and an inlet passage connectable to an inflation means, said valve body defining a valve chamber in which a flexible diaphragm is provided partially or substantially closing the chamber and said diaphragm having a deflation air-flow passage which on one side of the diaphragm is in communication with said inlet and outlet passage, and on an opposing side of the diaphragm, is in communication with an exhaust outlet or atmosphere and is closeable or partially closeable during deflation by a displaceable closure disc, plate or platen which is releasably held in a closing position against said diaphragm passage by a manually operable, controllable or adjustable release means, wherein the closure disc, plate or platen and diaphragm have an air escape passage or means which varies in cross-section as the deformation of the diaphragm due to the pressure difference across it and the position of the closure disc, plate or platen varies.

* * * * *